(12) United States Patent
Akeno et al.

(10) Patent No.: US 6,375,647 B1
(45) Date of Patent: Apr. 23, 2002

(54) DISPOSABLE DIAPER

(75) Inventors: Mitsuru Akeno; Yutaka Tominaga; Toshiaki Takizawa, all of Toyama-ken (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 09/629,267

(22) Filed: Jul. 31, 2000

(30) Foreign Application Priority Data

Aug. 12, 1999 (JP) .......................................... 11-228212

(51) Int. Cl.[7] .............................................. A61M 16/00
(52) U.S. Cl. ...................... 604/391; 604/389; 604/386; 604/387
(58) Field of Search ................................ 604/358, 367, 604/385.01, 385.03, 385.13, 385.21, 385.23, 385.24, 385.29, 385.3, 349, 346, 344, 385.28, 386, 387, 390, 391, 392, 394, 396; 24/437, 320, 374, 542, 575, 578, 580, 598.1, 610, 615

(56) References Cited

U.S. PATENT DOCUMENTS

| | | | | |
|---|---|---|---|---|
| 3,266,113 A | * | 8/1966 | Flanagan ..................... 24/204 |
| 3,408,705 A | * | 11/1968 | Kayser et al. ................. 24/204 |
| 3,808,648 A | * | 5/1974 | Billarant et al. .............. 24/204 |
| 4,216,257 A | * | 8/1980 | Schams et al. ................ 428/93 |
| 4,322,875 A | * | 4/1982 | Brown et al. .................. 24/204 |
| 4,894,060 A | * | 1/1990 | Nestegard .................... 604/391 |
| 5,221,276 A | * | 6/1993 | Battrell ....................... 604/389 |
| 5,269,776 A | | 12/1993 | Lancaster et al. ........... 604/387 |
| 5,342,344 A | * | 8/1994 | Lancaster et al. ........... 604/387 |
| 5,345,659 A | | 9/1994 | Allan .......................... 24/442 |
| 5,679,302 A | * | 10/1997 | Miller et al. ................. 264/167 |
| 5,860,194 A | * | 1/1999 | Takizawa et al. ............. 24/452 |
| 5,879,604 A | * | 3/1999 | Melbye et al. ............... 264/167 |
| 6,076,238 A | * | 6/2000 | Arsenault et al. ............. 24/252 |

* cited by examiner

Primary Examiner—John G. Weiss
Assistant Examiner—Jacqueline F Stephens
(74) Attorney, Agent, or Firm—Finnegan, Henderson, Farabow, Garrett & Dunner, L.L.P.

(57) ABSTRACT

The present invention provides a disposable diaper, which is easy to put on the wearer, and which is possible to be put on easily when the wearer is standing on both legs. The disposable diaper including a diaper body having a hip portion and a belly portion, which are spread out with a crotch portion between them. The disposable diaper includes engaging means, which are arranged to be attachable/detachable, on the both side portions of the hip portion and the belly portion. The engaging means have hook elements which are disposed on the hip portion and projecting toward the belly portion, engaging faces disposed on the hook elements and facing to the hip portion, hook elements which are disposed on the belly portion and projecting toward the hip portion and engaging faces disposed on the hook elements and which are facing to the belly portion. At least one of the hook elements is sandwiched between the hook elements, so that the engaging faces come into contact with each other to engage the hook elements each other.

3 Claims, 4 Drawing Sheets

DISPOSABLE DIAPER

BACKGROUND OF THE INVENTION

1. Field of the Invention

The present invention relates to a disposable diaper, which is disposed after use.

2. Description of the Related Art

As a conventional disposable diaper, a spread out type disposable diaper is designed with a hip portion to cover a wearer's hip and a belly portion to cover the wearer's belly. In this spread out type disposable diaper, the hip portion and the belly portion are spread apart and they are composed attachably/detachably. The spread out type disposable diaper comprises a sheet-shaped diaper body, which encloses an absorbent polymer or the like therein. When the wearer uses this diaper, the sheet-shaped diaper body is formed as a stereoscopic shape so that the diaper obtains a pants-like shape. In the spread out type disposable diaper, the diaper body is composed of the hip portion, a crotch portion and the belly portion provided integrally and continuously. At the both sides of the hip portion, adhesive tapes are disposed to extend to the outside. The adhesive tapes are held in tentative attaching portions made of a film or the like, which are provided on the hip portion before assembling the diaper. When the diaper is put on, the adhesive tapes are secured to the belly portion.

As for conventional disposable diapers, a pants-shaped diaper has been used. This pants-shaped disposable diaper is designed such that the wearer can put it on, as the wearer is standing. The wearer inserts his legs into leg-through holes from the inside to the outside of the diaper for each leg and the diaper can be pulled up to the wearer's waist, as if the wearer puts a pants on.

The conventional spread out type disposable diaper, which is provided with a hook shaped connecting member, is disclosed in Japanese Patent No. 2525779. This disposable diaper is provided with a first fastener member with a plate shape inside of both sides of a hip portion. This first fastener member is folded back toward the inside of the hip portion. Further, being opposed to the first fastener member at the both sides of an outside of a belly portion, a second fastener member of a plate shape is provided. This second fastener member is folded back toward the front side of the belly portion. In the first fastener member and the second fastener member, the respective folded portions extend away from a disposable diaper body, the respective medium portions curve toward the surface of the disposable diaper body and the respective front portions are folded away from the disposable diaper body. As a result, the first fastener member and the second fastener member become substantially in the shape of the letter S. In this conventional disposable diaper, the both sides of the hip portion and the belly portion are sufficiently overlapped to engage the first fastener member and the second fastener member, so that the disposable diaper body is formed in a stereoscopic shape.

In the foregoing conventional arts, the spread-out type disposable diaper can not worn while the wearer is standing. The wearer has to be laid to put the diaper on, which is laborious and also requires a space enough to lay the wearer down. Therefore, it is quite inconvenient at the time of going outside. The pants-shaped disposable diaper is designed such that the wearer can put it on, as the wearer is standing. However, the wearer inserts his legs into leg-through holes from the inside to the outside of the diaper, so it is difficult to put it on with shoes on.

On the other hand, according to the disposable diaper disclosed in Japanese Patent No. 2525779, when the first fastener number and the second fastener member are engaged, it is necessary to engage the both sides of the hip portion and the belly portion after pulling them up sufficiently till the first fastener member pass over the second fastener member. Therefore, force is needed and it gives a feeling of pressing to the wearer. Further, it is hard to attach the fastener members and to put on.

SUMMARY OF THE INVENTION

The present invention has been achieved taking the foregoing problem into consideration, an object of which is to provide a disposable diaper, which is easy for the wearer to put on and is possible to be put on easily when the wearer is standing on both feet.

The present invention provides a disposable diaper including a diaper body having a hip portion and a belly portion, which are spread out with a crotch portion between them, and engaging means, which are arranged to be engaged/disengaged with each other, on both side portions of the hip portion and both side portions of the belly portion. The engaging means includes a plurality of hook elements having rising portions provided on one surface at both ends portions of the hip portion and on the other surface at both end portions of the belly portion and engaging portions bending and extending at distal ends of the rising portions. At least one of the hook elements is sandwiched between opposed hook elements and the opposed engaging faces come into contact with each other, so that the hook elements are engaged each other.

Preferably, the hook elements are elongated substantially perpendicular to the direction around a waist of a wearer and have a regular cross-section substantially perpendicular to the longitudinal direction, the engaging faces of the hook elements are formed at least on the opposite side with respect to the end edges of the both side portions.

Further preferably, at least one group of the hook elements are provided with stopper portions formed by deforming the hook elements at the both end portions of the longitudinal direction of the hook elements.

According to the disposal diaper of the present invention, both side portions of the hip portion and both side portions of the belly portion are positioned at the outside of the wearer's legs so that the one group of the hook elements are pressed into other group of the hook elements. And the hook elements are elastically deformed each other, so that the one group of the hook elements are sandwiched between the other group of the hook pieces. At this time, the engaging faces defined on each group of the hook elements come into contact with each other to be fastened. Thus, in the disposable diaper of the present invention, the pair of leg-through holes are made with the wearer's legs inserted into the leg-through holes. Therefore, the disposable diaper of the present invention can be formed in a stereoscopic shape for use. With the wearer's his legs inserted into the holes, it is possible to pull up the disposable diaper to the wearer's waist.

DESCRIPTION OF THE PREFERRED EMBODIMENTS

Figure 1:
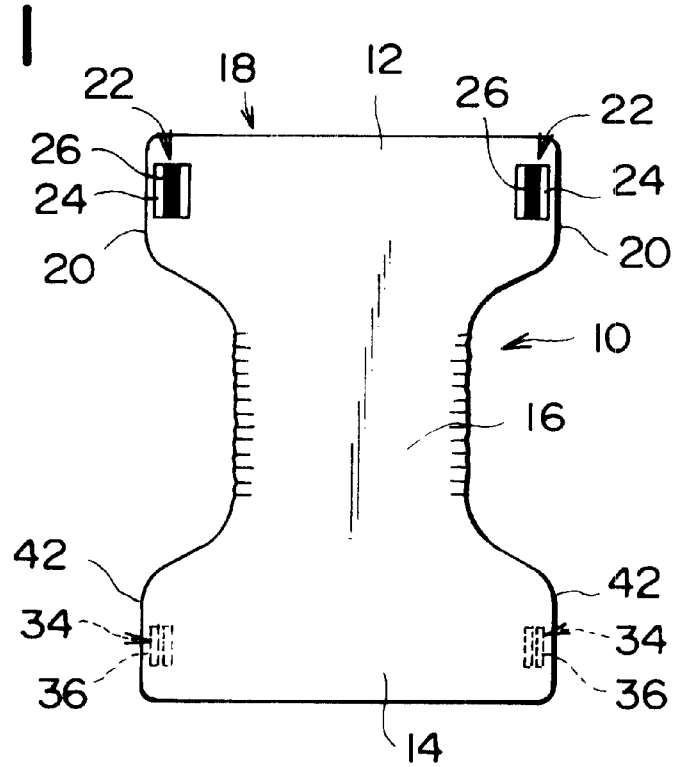
FIG. 1 is a plan view of a disposable diaper according to an embodiment of the present invention.

Embodiments of the present invention will be explained below with reference to the drawings. FIGS. 1 to 4 illustrate an embodiment of the present invention. A disposable diaper 10 according to this embodiment of the present invention comprises a diaper body 18, which is composed integrally with a hip portion 12 to cover the wearer's hip, a belly portion 14 to cover the wearer's belly and a narrow crotch portion 16 to be positioned between the hip portion 12 and the belly portion 14. The diaper body 18 is configured such that a waterproof cover sheet is provided on the outside thereof and an absorbent body made of an absorbent polymer is disposed on the inside, namely, the side which the body touches. Further, a liquid-permeable sheet is disposed on the surface of the absorbent body. FIG. 1 shows the disposable diaper 10 with a view of the outside of the diaper body 18, namely, showing the cover sheet.

Figure 2:
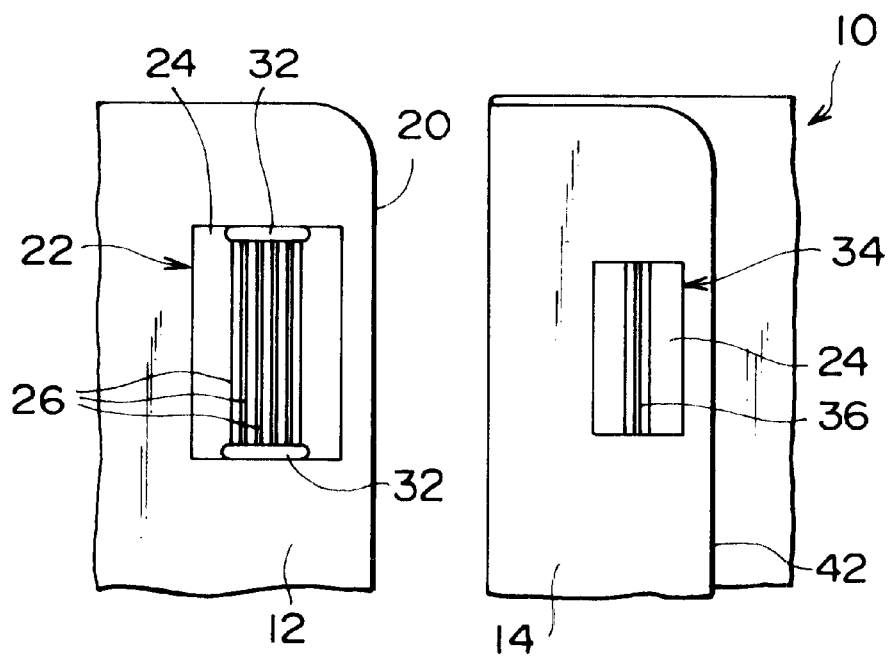
FIG. 2 is a partial plan view of both side portions of the disposable diaper according to the present embodiment.
Figure 3:
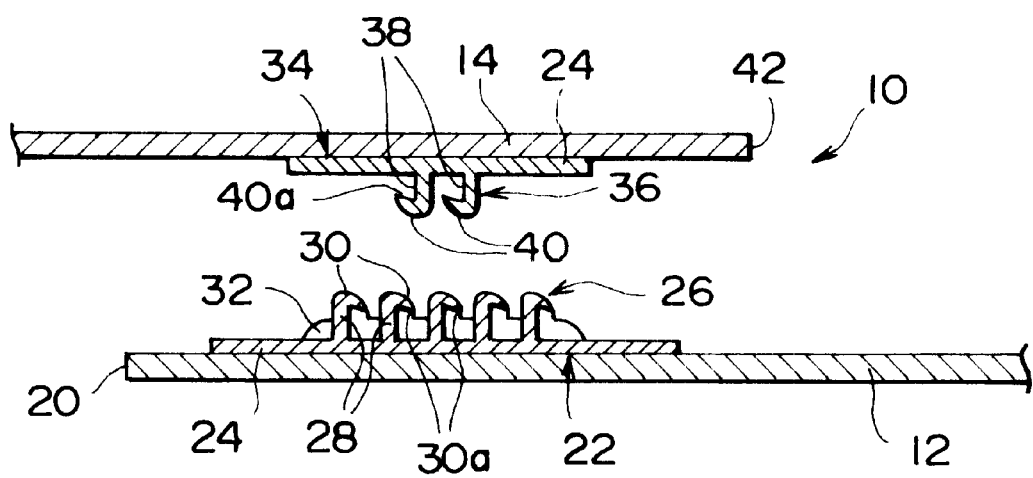
FIG. 3 is a cross sectional view for illustrating a state in which the both side portions of the disposable diaper according to the present embodiment are about to be connected.

The disposal diaper 10 is provided with engaged members 22, which are engaging means made of synthetic resin with appropriate elastic force, on the outside of the hip portion 12 and in both side portions 20. The engaged members 22 are provided with five rows of hook elements 26 on base plates 24 as shown in FIG. 2, the hook elements 26 projecting to make lines. The hook elements 26 are in parallel with end edges of both side portions 20 and are provided at even intervals. A sectional shape, perpendicular to a longitudinal direction, of each of hook elements 26 shows a rising portion 28, which is rising substantially perpendicular to the base plate 24 as shown in FIG. 3. First engaging portions 30 are formed integrally with the front end of the rising portion 28, to project to the opposite side of the both side portions 20. On the face of each first engaging portion 30, which faces to the hip portion 12, an engaging face 30a is composed. On both end portions in the longitudinal direction of the hook elements 26, stopper portions 32 are provided, respectively. The stopper portions 32 are formed by fusing and pressing down the hook elements 26 on the surface of the base plate 24 by heating means.

Engaging members 34 are disposed, which are engaging means with appropriate elastic force, at the inside of the belly portion 14 and in both side portions 42. The engaging members 34 are provided with two rows of hook elements 36 projecting in lines on the base plate 24. The hook elements 36 are in the same shape as that of the hook elements 26 disposed on the engaged member 22 of the hip portion 12. The hook elements 36 has a rising portion 38, which is rising substantially perpendicular to the base plate 24. First engaging portions 40, which project to the opposite side of end portions of the both side portions 42, are formed integrally with front ends of the rising portions 38. On the face of the first engaging portions 40, which faces to the belly portion 14, engaging faces 40a are formed. The above described engaged member 22 and the engaging member 34 can be obtained by cutting a molded member in a sheet shape to have a desired length in a longitudinal direction. The molded member is continuously molded integrally by extrusion molding of synthetic resin material. Further, in the engaged member 22, by heat-cutting the sheet shaped molded member, the stopper portions 32 are formed easily at the same time of cutting.

Figure 4:
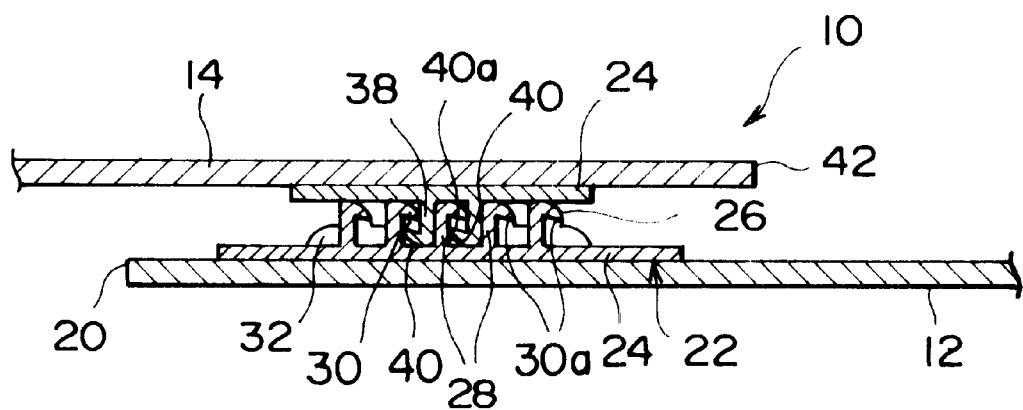
FIG. 4 is a cross sectional view for illustrating a state in which the both side portions of the disposable diaper according to the present embodiment are connected.

A method for using the disposable diaper 10 according to the present embodiment will be explained below. Firstly, as an infant who is the wearer is standing, the crotch portion 16 of the diaper body 18 is positioned between both feet near the bottom of the feet of the wearer. Both side portions 20 of the hip portion 12 and both side portions 42 of the belly portion 14 are overlapped at the outside of wearer's crotch. The hook elements 36 of the engaging members 34 of the belly portion 14 are pressed into the hook elements 26 of the engaged members 22 of the hip portion 12. Therefore, the hook elements 36 and 26 are elastically deformed so that the first engaging portions 40 of the hook elements 36 clime over the first engaging portions 30 of the hook elements 26. Consequently, the engaging faces 30a of the first engaging portions 30 and the engaging faces 40a of the first engaging portions 40 come into contact with each other to be engaged as shown in FIG. 4. As a result, in the diaper body 18, the both side portions 20 of the hip portion 12 and both side portions 42 of the belly portion 14 are connected each other at the outside of the wearer's crotch. Accordingly, the diaper body 18 obtains a stereoscopic shape for the use. At this time, the wearer's legs are in leg-through holes, which are defined by bending the diaper body 18. In this state, the disposable diaper 10 can be pulled up to the waist of the wearer.

According to the disposable diaper 10 of the present embodiment, it is possible to easily form the spread out type diaper into a stereoscopic shape while the wearer is standing. Since the engaging members 34 and the engaged members 22 can be engaged reliably and can be connected firmly due to the elastic force of the synthetic resin, so that the spread out type diaper of the present embodiment can be pulled up to the waist of the wearer like a pants type diaper. Further, when assembling the disposable diaper 10, the leg-through holes can be defined as the wearer is standing with his legs being inserted into the holes. Therefore, with the wearer's shoes on, it is possible to put on the disposable diaper 10 easily. When the wearer puts on the disposable diaper 10 outdoors, sand or the like does not enter the diaper. The engaging members 22 are provided with the stopper members 32 at the both end portions thereof in the longitudinal direction of the hook elements 26, so that the hook elements 36 of the engaging members 34 are not displaced vertically during the use of the disposable diaper 10. Further when putting on the disposable diaper 10, the relative positioning of the height of the hip portion 12 and the belly portion 14 can be reliably performed. Therefore, it is easy to form the disposable diaper 10 into the appropriate shape. Since five parallel rows of the hook elements 26 of the engaged members 22 are disposed on the both side portions 20 of the hip portion 12, it is possible to adjust the engaging positions of the engaging members 34 in conformity to the waist size of the wearer.

Figure 5:
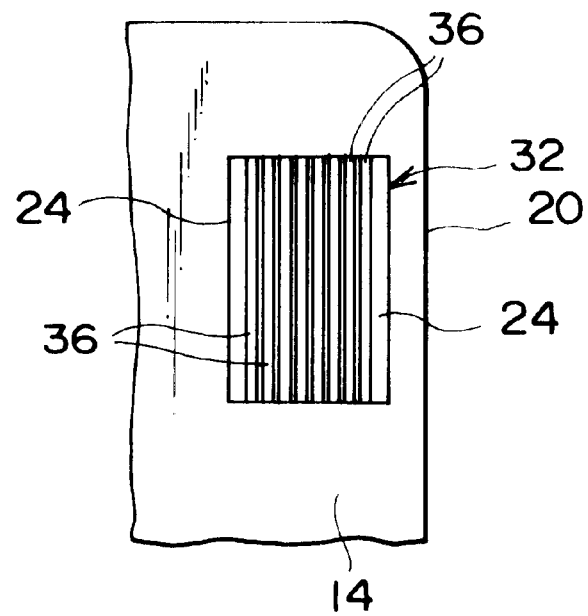
FIG. 5 is a plan view of a modification of an engaged member of the disposable diaper according to the present embodiment.

The disposable diaper according to the present invention may not be limited to each embodiment as set forth above. For example, as shown in FIG. 5, the disposable diaper according to the present invention may have no stopper portions on the engaged members 22. Further, the number of the hook elements 26 may not be limited to five, but any number such as eight may be available. The engaging means may be disposed on either front side or rear side of either the hip portion or the belly portion.

Figure 6:
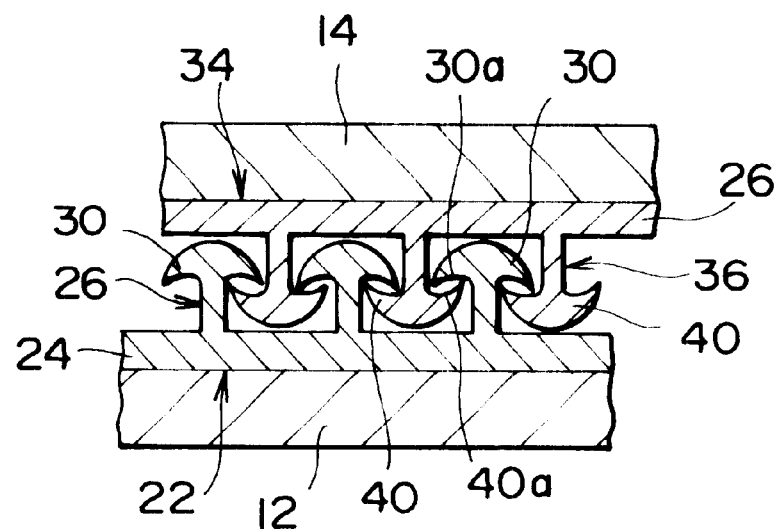
FIG. 6 is a cross sectional view of a modification of an engaging member and the engaged member of the disposable diaper according to the present embodiment.

Further, in the disposable diaper according to the present invention, the number or the shape of the hook elements can be alternated freely. As shown in FIG. 6, the disposable diaper may be provided with the engaged members 22 and the engaging members 34 such that the hook elements 26 and 36 with T-shaped sections which have first engaging portions 30 and 40 projecting to the both sides are provided thereto. Accordingly, the hook elements 26 and 36 engage more firmly and they are hardly disengaged.

Figure 7:
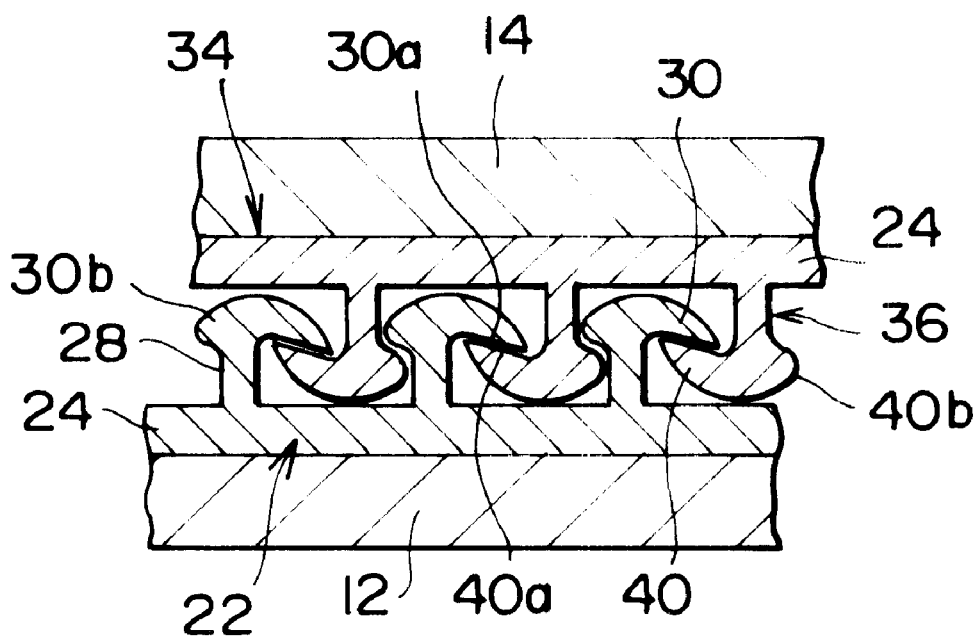
FIG. 7 is a cross sectional view of a modification of the engaging member and the engaged member of the disposable diaper according to the present embodiment.

Also, as shown in FIG. 7, the disposable diaper may be provided with second engaging projections 30b and 40b, which are slightly projecting to the side portion, on the opposite side of the first engaging portions 30 and 40 of the hook elements 26 and 36. In this case, the hook elements 26 and 36 engage more firmly. In this case, it is rather easy to disengage the hook elements 26 and 36.

Further, the engaging projections may project to the reverse direction to that of the present embodiment. Appropriate pick up pieces may be provided on the engaging members on both sides of the belly portion. As a result, it becomes easier to disengage the engaging members from the engaged members by the pick up pieces. Further, the wearer of the disposable diaper according to the present invention may be a baby or an adult. The disposable diaper according to the present invention may be put on the wearer who is standing or is laid.

The disposable diaper of the invention is convenient since it is easy to put on the wearer when the wearer is standing on both legs. When the diaper is formed as a stereoscopic shape, the hip portion and the belly portion are firmly connected to each other at correct portions. Further, engagement is secured and if the wearer moves hard, they will not get disengaged.

What is claimed is:
1. A disposable diaper comprising:
   a diaper body having a hip portion with two side portions having an edge and a belly portion with two side portions having an edge, which are spread out with a crotch portion between them, and
   engaging means, which are arranged to be engaged/disengaged with each other, on both side portions of the hip portion and both side portions of the belly portion;
      wherein said engaging means comprise a base plate provided on one surface at both side portions of said hip portion and on one surface at both side portions of said belly portion, and a plurality of linearly elongated hook elements having rising portions rising from said base plate and engaging portions bending and extending at distal ends of said rising portions, each said hook elements extending to be continuous along substantially the entire length of said base plate; and
      wherein at least one of said hook elements is sandwiched between opposed hook elements and their opposed engaging faces come into contact with each other, so that said hook elements are engaged with each other.
2. A disposable diaper according to claim 1, wherein said hook elements are elongated substantially perpendicular to the waist of a wearer and have a regular cross section substantially perpendicular to a longitudinal direction of said hook, said engaging faces of said hook elements are formed at least on the side of the hook elements opposite the edge of the side portions.
3. A disposable diaper according to claim 1, wherein at least one group of said hook elements are provided with stopper portions formed by deforming said hook elements at both end portions of the longitudinal direction of said hook elements.

* * * * *

UNITED STATES PATENT AND TRADEMARK OFFICE
CERTIFICATE OF CORRECTION

PATENT NO. : 6,375,647 B1
DATED : April 23, 2002
INVENTOR(S) : Mitsuru Akeno et al.

It is certified that error appears in the above-identified patent and that said Letters Patent is hereby corrected as shown below:

<u>Title page,</u>
Item [54], after "DIAPER", insert -- WITH HOOK FASTENING ELEMENTS --

Item [57], ABSTRACT,
Line 18, "elements each" should read -- elements with each --

Signed and Sealed this

Eighth Day of October, 2002

*Attest:*

*Attesting Officer*

JAMES E. ROGAN
*Director of the United States Patent and Trademark Office*